US00PP20581P2

(12) United States Plant Patent
Batson

(10) Patent No.: US PP20,581 P2
(45) Date of Patent: Dec. 15, 2009

(54) ***ILEX* PLANT NAMED 'SCARLET'S PEAK'**

(50) Latin Name: *Ilex vomitoria*
Varietal Denomination: Scarlet's Peak

(75) Inventor: Daniel B. Batson, Perkinston, MS (US)

(73) Assignee: Unique Plants Inc., Perkinston, MS (US)

( * ) Notice: Subject to any disclaimer, the term of this patent is extended or adjusted under 35 U.S.C. 154(b) by 0 days.

(21) Appl. No.: 12/287,350

(22) Filed: Oct. 8, 2008

(51) Int. Cl.
*A01H 5/00* (2006.01)

(52) U.S. Cl. ..... Plt./247

(58) Field of Classification Search ..... Plt./247
See application file for complete search history.

*Primary Examiner*—Susan B McCormick Ewoldt
(74) *Attorney, Agent, or Firm*—C. A. Whealy

(57) ABSTRACT

A new and distinct cultivar of *Ilex* plant named 'Scarlet's Peak', characterized by its upright and fastigiate plant form; dense and bushy growth habit; dark green-colored leaves; and good garden performance.

2 Drawing Sheets

Botanical designation: *Ilex vomitoria.*
Cultivar denomination: 'Scarlet's Peak'.

BACKGROUND OF THE INVENTION

The present Invention relates to a new and distinct cultivar of *Ilex*, botanically known as *Ilex vomitoria*, commercially known as Yaupon Holly and hereinafter referred to by the name 'Scarlet's Peak'.

The new *Ilex* is the product of a chance open-pollination of an unnamed selection of *Ilex vomitoria*, not patented, as the female, or seed, parent with an unknown selection of *Ilex vomitoria* as the male, or pollen, parent. The new *Ilex* plant was discovered and selected by the Inventor in July, 2005 from within the resulting progeny from the stated open-pollination in a controlled outdoor nursery environment in Perkinston, Miss. The selection of the new *Ilex* was based on its fastigiate plant form.

Asexual reproduction of the new *Ilex* plant by stem cuttings in Perkinston, Miss. since October, 2005 has shown that the unique features of this new *Ilex* plant are stable and reproduced true to type in successive generations of asexual reproduction.

SUMMARY OF THE INVENTION

Plants of the new *Ilex* have not been observed under all possible environmental conditions. The phenotype may vary somewhat with variations in environment such as temperature and/or light intensity without, however, any variance in genotype.

The following traits have been repeatedly observed and are determined to be the unique characteristics of 'Scarlet's Peak'. These characteristics in combination distinguish 'Scarlet's Peak' as a new and distinct cultivar of *Ilex:*

1. Upright and fastigiate plant form.
2. Dense and bushy growth habit.
3. Dark green-colored leaves.
4. Good garden performance.

Plants of the new *Ilex* can be compared to plants of the female parent selection. Plants of the new *Ilex* differ from plants of the female parent selection in the following characteristics:

1. Plants of the new *Ilex* are more upright and fastigiate than plants of the female parent selection.
2. Young stems of plants of the new *Ilex* are thinner and more flexible than young stems of plants of the female parent selection.

Plants of the new *Ilex* can be compared to the plants of *Ilex vomitoria* 'Will Flemming', not patented. In side-by-side comparisons conducted in Perkinston, Miss., plants of the new *Ilex* differed from plants of 'Will Flemming' in the following characteristics:

1. Plants of the new *Ilex* were more fastigiate in plant form than plants of 'Will Flemming'.
2. Plants of the new *Ilex* had stronger stems than plants of 'Will Flemming'.
3. Plants of the new *Ilex* produced only female flowers whereas plants of 'Will Flemming' produced only male flowers.

BRIEF DESCRIPTION OF THE PHOTOGRAPHS

The accompanying colored photographs illustrate the overall appearance of the new *Ilex*. These photographs show the colors as true as it is reasonably possible to obtain in colored reproductions of this type. Colors in the photographs may differ slightly from the color values cited in the detailed botanical description, which accurately describe the colors of the new *Ilex*.

The photograph on the first sheet comprises a side perspective view of a typical plant of 'Scarlet's Peak' grown in a container in an outdoor nursery.

The photograph on the second sheet is a close-up view of typical leaves and developing fruits of 'Scarlet's Peak'.

DETAILED BOTANICAL DESCRIPTION

The aforementioned photographs and following observations and measurements describe plants grown in Perkinston, Miss. in an outdoor nursery and under commercial production conditions. During the production of the plants, day temperatures ranged from 7° C. to 37° C. and night temperatures ranged from −9° C. to 20° C. Plants used for the photographs and description had been growing for three years. In the following description, color references are made to The Royal Horticultural Society Colour Chart, 1995 Edition, except where general terms of ordinary dictionary significance are used.

Botanical classification: *Ilex vomitoria* 'Scarlet's Peak'.

Parentage:

*Female, or seed, parent.*—Unnamed selection of *Ilex vomitoria*, not patented.

*Male, or pollen, parent.*—Unknown selection of *Ilex vomitoria*, not patented.

Propagation:

*Type.*—By stem cuttings.

*Time to initiate roots, summer.*—About four weeks at temperatures of 30° C. to 35° C.

*Time to initiate roots, winter.*—About seven weeks at temperatures of 12° C. to 18° C.

*Time to produce a rooted young plant, summer.*—About two months at temperatures of 30° C. to 35° C.

*Time to produce a rooted young plant, summer.*—About four months at temperatures of 12° C. to 18° C.

*Root description.*—Medium in thickness, fibrous; white in color.

*Rooting habit.*—Freely branching; moderately dense.

Plant description:

*Plant form and growth habit.*—Perennial evergreen shrub; upright and fastigiate plant form.

*Branching habit.*—Freely branching habit; dense and bushy growh habit with numerous lateral branches developing per plant.

*Plant height.*—About 3 meters.

*Lateral branch description.*—Length: About 30 cm to 45 cm. Diameter: About 8.2 mm to 13.3 mm. Internode length: About 5.2 mm to 11.7 mm. Strength: Strong, flexible. Texture: Smooth, glabrous. Color, young stems: Close to 59A. Color, mature stems: Close to 199A.

*Foliage description.*—Arrangement: Alternate, simple. Length: About 23.1 mm to 25.5 mm. Width: About 9.5 mm to 11.9 mm. Shape: Oblong to ovate. Apex: Bluntly acute. Base: Obtuse. Margin: Serrulate. Venation pattern: Pinnate, reticulate. Texture, upper and lower surfaces: Smooth, glabrous. Color: Developing leaves, upper surface: Close to 146A. Developing leaves, lower surface: Close to 146B. Fully expanded leaves, upper surface: Close to 147A; venation, close to 147A. Fully expanded leaves, lower surface: Close to 147B; venation, close to 147B. Petiole: Length: About 2.7 mm to 3.1 mm. Diameter: About 0.7 mm to 1.1 mm. Texture, upper and lower surfaces: Smooth, glabrous. Color, upper and lower surfaces: Close to 147A to 147B.

Flower description:

*Flower arrangement and appearance.*—Single cruciform flowers arranged in fascicles of three.

*Natural flowering season.*—Plants of the new *Ilex* typically flower during the spring in Mississippi.

*Flower longevity.*—Individual flowers last several days on the plant; flowers persistent.

*Fragrance.*—None detected.

*Flower diameter.*—About 4 mm.

*Flower depth.*—About 2 mm.

*Flower bud.*—Length: About 1.5 mm. Diameter: About 1.5 mm. Shape: Spherical. Color: Close to 155D.

*Petals.*—Arrangement: Single cruciform flower form; single whorl of four petals fused at the base. Length: About 2 mm. Width: About 1 mm. Shape: Oblong. Apex: Rounded. Margin: Entire. Texture, upper and lower surfaces: Smooth, glabrous; waxy. Color: When opening and fully opened, upper surface: Close to 155D. When opening and fully opened, lower surface: Close to 155D.

*Sepals.*—Arrangement: Four fused in a single whorl; calyx, campanulate. Length: About 0.7 mm. Width: About 0.9 mm. Shape: Awl-shaped. Apex: Acute. Texture, upper and lower surfaces: Smooth, glabrous; waxy. Color, upper and lower surfaces: Close to 145B to 145C.

*Peduncles.*—Length: About 2 mm. Diameter: About 0.5 mm. Angle: About 45° from lateral branch axis. Strength: Strong, flexible. Texture: Smooth, glabrous. Color: Close to 145B.

*Reproductive organs.*—Androecium: No male reproductive structures observed. Gynoecium: Pistil length: About 1.5 mm. Stigma shape: Blunted. Stigma color: Close to 145B. Style length: About 1 mm. Style color: Close to 145B. Ovary color: Close to 145B.

*Fruits.*—Quantity per plant: About 20 to 35 per lateral branch. Length: About 5.7 mm. Diameter: About 5.7 mm. Texture: Smooth, glabrous. Color, immature: Close to 144A. Color, mature: Close to 44B.

*Seeds.*—Quantity per fruit: About four. Length: About 4.8 mm. Diameter: About 2.3 mm.

Garden performance: Plants of the new *Ilex* have been observed to have good garden performance and to be tolerant to rain, wind and temperatures ranging from about −15° C. to about 38° C.

Disease/pest resistance: Plants have not been observed to be resistant to pathogens and pests common to *Ilex*.

It is claimed:

1. A new and distinct cultivar of *Ilex* plant named 'Scarlet's Peak' as illustrated and described.

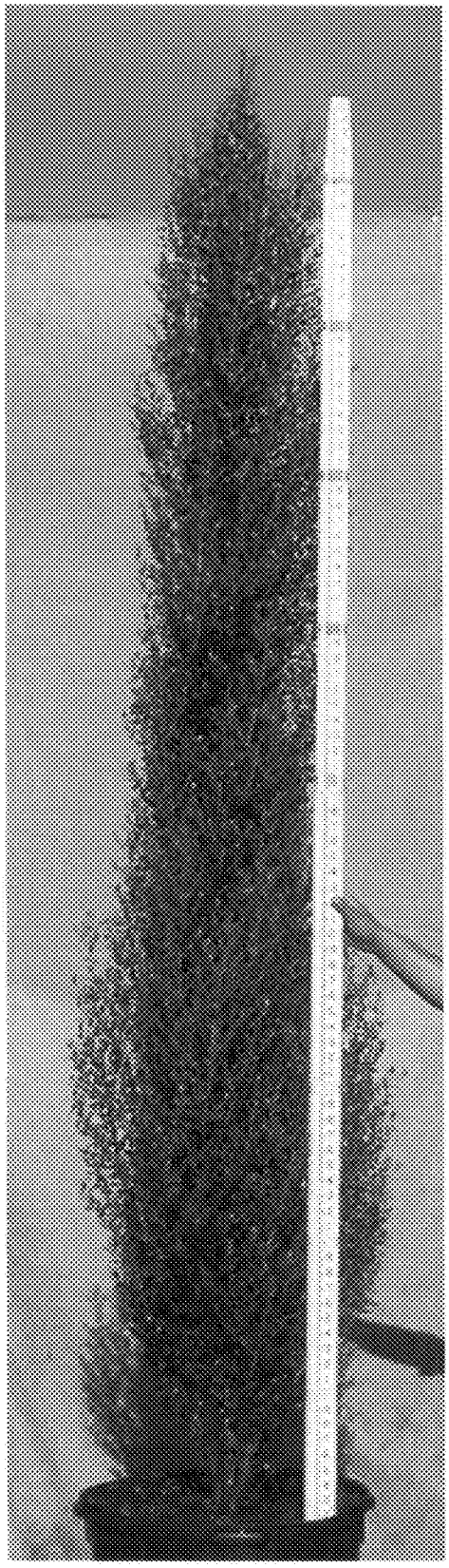

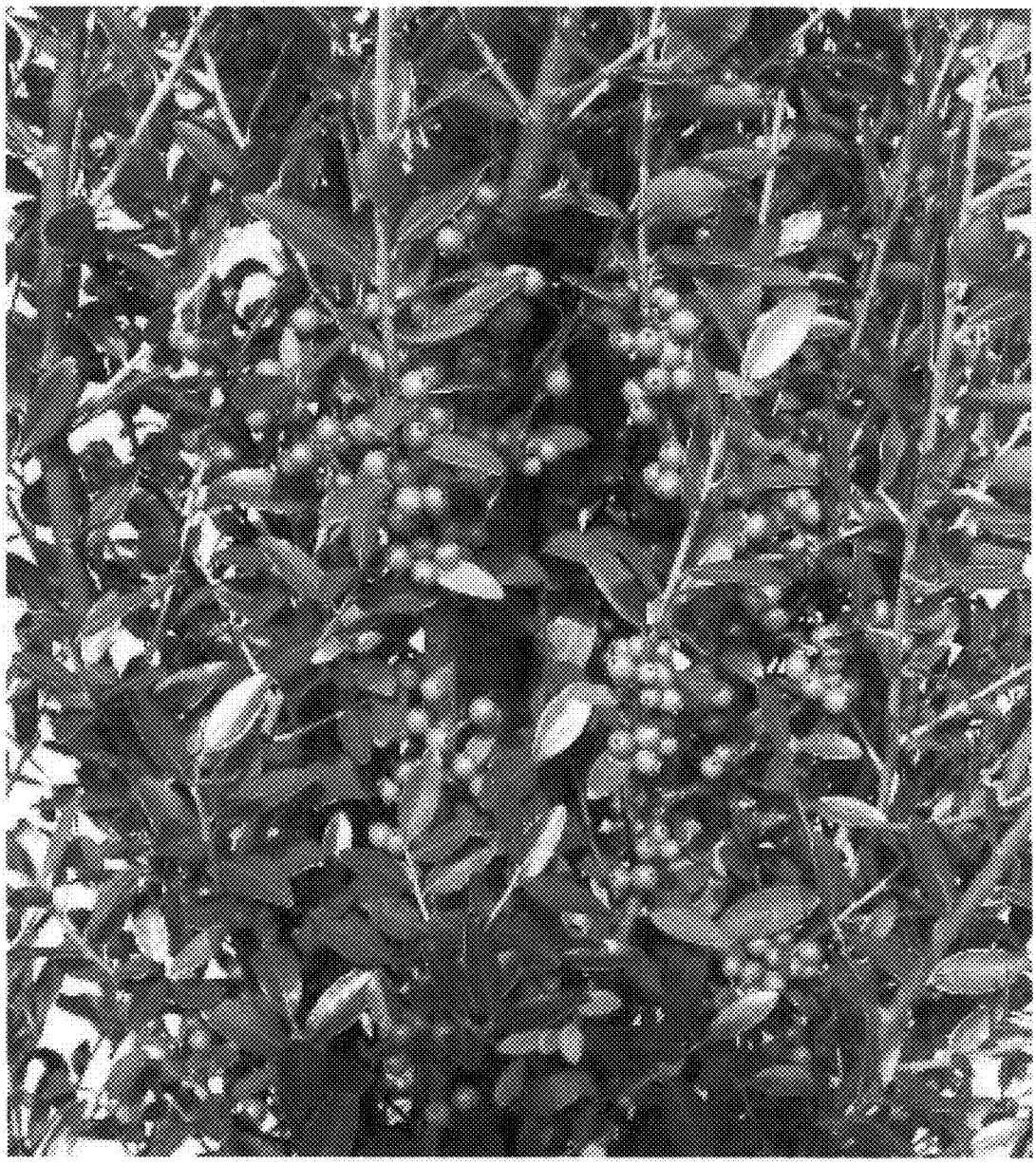

* * * * *